United States Patent [19]
Giele et al.

[11] Patent Number: 5,575,814
[45] Date of Patent: Nov. 19, 1996

[54] ACTIVE FIXATION MEDICAL ELECTRICAL LEAD HAVING MAPPING CAPABILITY

[75] Inventors: Vincent Giele, Wilheiminadorp, Netherlands; Kenneth B. Stokes, Elk River; Mary M. Morris, Mounds View, both of Minn.

[73] Assignee: Medtronic, Inc., Minneapolis, Minn.

[21] Appl. No.: 379,826

[22] Filed: Jan. 27, 1995

[51] Int. Cl.$^6$ .................................................. A61N 1/05
[52] U.S. Cl. ........................................ 607/127; 607/120
[58] Field of Search ............................. 607/119, 120, 607/122, 126–128, 130, 131; 128/642

[56] References Cited

U.S. PATENT DOCUMENTS

| | | |
|---|---|---|
| 4,106,512 | 8/1978 | Bisping . |
| 4,146,036 | 3/1979 | Dutcher et al. . |
| 4,217,913 | 8/1980 | Dutcher . |
| 4,233,992 | 11/1980 | Bisping . |
| 4,282,885 | 8/1981 | Bisping . |
| 4,570,642 | 2/1986 | Kane et al. . |
| 4,649,938 | 3/1987 | McArthur . |
| 4,667,686 | 5/1987 | Peers-Travarton . |
| 4,886,074 | 12/1989 | Bisping . |
| 5,003,992 | 4/1991 | Holleman et al. . |
| 5,259,395 | 11/1993 | Li .................................................. 607/131 |
| 5,314,461 | 5/1994 | Borghi ............................................ 607/127 |

FOREIGN PATENT DOCUMENTS 0422363  8/1990  European Pat. Off. .......... A61N 1/05

*Primary Examiner*—William E. Kamm
*Assistant Examiner*—Jeffrey R. Jastrzab
*Attorney, Agent, or Firm*—Michael J. Jaro; Harold R. Patton

[57] ABSTRACT

A body-implantable transvenous endocardial lead for an implantable medical device system. The lead includes inner and outer coiled conductors each surrounded by a flexible elongate sheath such that the inner conductor is rotatable within the outer sheath. An electrode assembly disposed at the distal end of the lead includes a distally-projecting fixation helix. A sliding member in the electrode assembly includes a helix-engaging collar for engaging the coils of the fixation helix, such that when the helix is rotated in a first direction with respect to the sliding member, it is advanced in a screw-like fashion distally forward with respect to the sliding member, and when the helix is rotated in a second direction with respect to the sliding member, it is retracted proximally backward with respect to the sliding member. A tip electrode is disposed on the distal end of the sliding member. When the helix is fully retracted, the helix-engaging collar is disposed substantially at the distal end of the helix such that the tip electrode extends distally beyond the distal end of the helix. When the helix is fully advanced, the helix engaging collar and the electrode are positioned substantially within the helix.

5 Claims, 6 Drawing Sheets

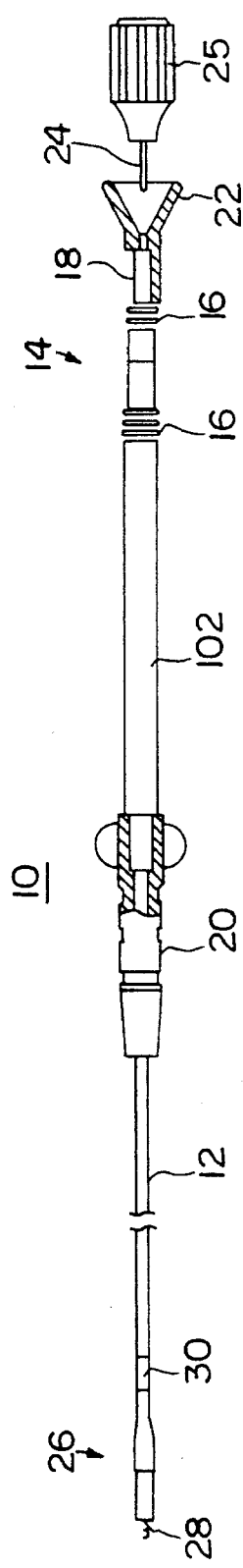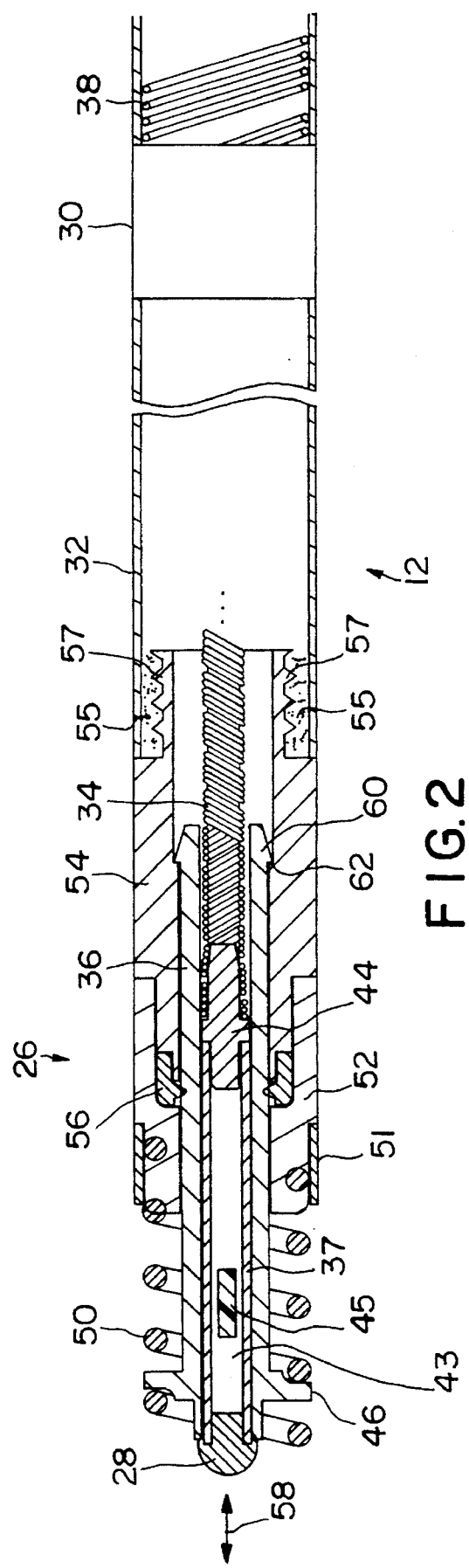

ACTIVE FIXATION MEDICAL ELECTRICAL LEAD HAVING MAPPING CAPABILITY

FIELD OF THE INVENTION

This invention relates generally to the field of medical electrical leads, and more particularly to an active fixation medical electrical lead having mapping capability.

BACKGROUND OF THE INVENTION

In the medical field, various types of body-implantable electrical leads are known and used. Particularly in the field of cardiac pulse generators, the use of implanted pacing and/or sensing leads is very common. Implantable cardiac pulse generators are typically implanted either in the region of a patient's thorax, for example under the skin near the patient's left or right clavicle, or in the patient's abdomen. A pacemaker lead, having a proximal end coupled to the pulse generator and a distal end that is in electrical contact with the patient's heart muscle, functions to convey electrical cardiac signals to sensing circuitry associated with the pulse generator, and/or to convey electrical stimulating pulses (e.g., pacing pulses) to the cardiac muscle from the pulse generator.

For endocardial leads, where the electrode tip of the lead is firmly lodged in or against endocardial tissue and chronically secured thereto in some fashion, the lead assembly is typically introduced through a body vessel, such as a vein, into one or more cardiac chambers. The conductor within the lead is protected by a biocompatible insulating material. A stylet may be provided for improving the maneuverability of the lead when inserted into, and guided through, the veins for positioning in the desired heart chamber. Examples of conventional endocardial leads in the prior art include: U.S. Pat. No. 3,348,548 to Chardack; U.S. Pat. No. 3,754,555 to Schmitt; U.S. Pat. No. 3,814,104 to Irnich et al.; U.S. Pat. No. 3,844,292 to Bolduc; and U.S. Pat. No. 3,974,834 to Kane.

Among the desirable attributes of endocardial leads are: minimal lead diameter; secure fixation of the electrode to cardiac tissue to prevent electrode dislodgement; implantation control with minimal damage to the vein, heart valves, cardiac tissue, or other tissue with which the electrode and lead come into contact; control of the fixation process to avoid excessive damage of tissue by the fixation mechanism; minimal electrical threshold; and maximal pacing impedance.

Another desirable attribute relates to the ability to bring a lead's electrode into temporary contact with a potential fixation site during lead introduction, so the electrical suitability of the selected site can be assessed prior to permanent (chronic) fixation of the electrode at the selected site. This function is commonly referred to as "mapping."

A lead's mappability is determined primarily by the configuration of the electrode assembly during transvenous introduction of the lead. For example, if a lead's electrode is required to be maintained in some type of retracted condition during lead introduction (as for leads whose sharp helical coil serves both as the fixation mechanism and the electrode), that lead's mappability will be poor since the electrode must be extended out from its retracted position before it can make electrical contact at the proposed implant site. For "screw-in" leads, often the suitability of a proposed fixation site cannot be fully assessed until the lead is screwed in to the tissue. In this case, if a site is found to be unsuitable, the lead must be unscrewed and a new site selected before the assessment process can proceed. This is undesirable because it increases the time necessary to perform a lead introduction procedure and also can result in tissue damage arising out of affixing the electrode at a site subsequently found to be unsuitable.

SUMMARY OF THE INVENTION

The present invention comprises a low-threshold, high-impedance, screw-in endocardial pacing lead. A distal electrode assembly is disposed on the distal end of the flexible elongate lead body. The lead body consists of two coaxial, elongate flexible sheaths, inner and outer. A first coiled conductor extends along the length the lead body within the lumen of the inner sheath, while a second coiled conductor extends along the length of the lead body within the lumen of the outer sheath, but around the outside of the inner sheath, such that the two conductors are mutually isolated from one another. The lead body's two conductors are rotatable with respect to one another about their common longitudinal axis, i.e., the inner coiled conductor can be relatively rotated with respect to the outer coiled conductor or the lead body outer sheath or both.

The electrode assembly includes a rigid, substantially cylindrical sleeve with a collar formed substantially near its distal end. The sleeve supports a conductive electrode substrate having a porous, platinized sintered electrode deposited on the distal end thereof which extends distally beyond the end of the sleeve.

The electrode fixation mechanism comprises a sharpened helix which engages the collar of the cylindrical sleeve, such that rotation of the helix with respect to the collar and sleeve causes the helix to advance or retract with respect to the collar and sleeve, due to the screw-like engagement of the helix and collar. The helix is thus advanceable to a fully advanced position wherein it extends distally beyond the end of the lead and electrode, such that the electrode is disposed within the coils of the helix. Likewise, the helix is retractable to a fully retracted position wherein the collar is disposed substantially at the distal end of the helix and wherein the electrode extends beyond the distal end of the helix. Introduction of the lead into a patient's venous system and mapping of potential fixation sites are facilitated with the helix in the fully retracted position, such that the collar surrounds the distal end of the helix to prevent the helix from snagging or tearing venous tissue during the lead introduction procedure. Also, with the helix in this fully retracted position, the electrode is exposed at the distal end of the lead, facilitating mapping of potential fixation sites. During fixation, the fixation helix advances and screws into the endocardium, leaving the electrode in contact with the myocardium.

BRIEF DESCRIPTION OF THE DRAWINGS

The above-described and other aspects of the present invention may be better understood and appreciated with reference to a detailed description of a specific embodiment of the invention, when read in conjunction with the accompanying drawings, wherein:

FIG. 1 is a plan view one embodiment of the invention;

FIG. 2 is an enlarged cross-sectional view of a distal section of the lead shown in FIG. 1 showing the fixation helix in a fully retracted position;

Figure 3:
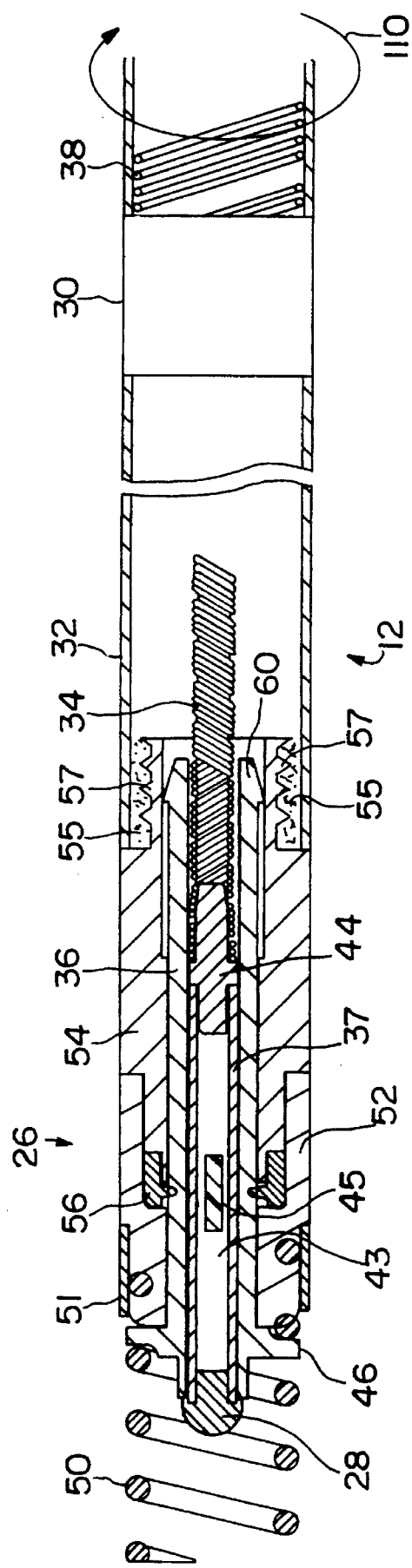
FIG. 3 is an enlarged cross-sectional view of the distal section of the lead shown in FIG. 1 showing the fixation helix in a fully advanced position.

The FIGS. are not necessarily to scale.

DETAILED DESCRIPTION OF THE INVENTION

The present invention will be described herein in connection with a bipolar transvenous lead adapted for use in connection with an implantable cardiac pulse generator, such as the Medtronic Legend™ or other models commercially available from Medtronic, Inc., Minneapolis, Minn.. It is to be understood, however, the disclosed embodiment is merely illustrative of various features and principles of the present invention and may be advantageously practiced in conjunction with many different types of implantable medical devices. It is believed those of ordinary skill in the art having the benefit of the present disclosure would be able to adapt the present invention to various applications, not limited to the particular bipolar pacing lead described herein.

Referring to FIG. 1, there is a plan view of a stylet-actuated, steroid eluting, screw-in endocardial bipolar pacing lead 10 constructed in accordance with one embodiment of the present invention. Lead 10 comprises a flexible, elongate lead body 12 which is covered by an insulative sleeve of flexible biocompatible and biostable insulating material, such as polyurethane or silicone rubber. At the proximal end of lead body 12, a terminal assembly 14 is provided for coupling lead 10 to an implantable pulse generator (not shown.) Terminal assembly 14 is provided with sealing rings 16 and a terminal pin 18, to be described herein in further detail, for connecting lead 10 to a pulse generator via a conventional connector block, such as the industry standard IS-1 Bi bipolar connector block, for example.

Anchoring sleeve 20 (shown partially in cross-section) is provided on lead body 12 for suturing lead body 12 to body tissue at the insertion point of lead 10 in a fashion known in the art. Anchoring sleeve 20 and terminal assembly 14 are preferably fabricated from silicone rubber, although they may also be constructed of any other suitable biocompatible material known in the art.

Lead 10 as shown in FIG. 1 further may also include a styler guide 22 and styler assembly 24 coupled to terminal pin 18 for imparting stiffness to lead 10 during the insertion and placement of lead 10 and for actuation of the lead's active fixation, as will be described herein in greater detail. Stylet guide 22 and stylet assembly 24 are discarded after use and before connection of terminal pin 18 to a pacemaker pulse generator.

With continued reference to FIG. 1, an electrode and fixation assembly 26 (also to be described herein in greater detail) is disposed at the distal end of lead body 12. Electrode and fixation assembly 26 is, in the disclosed embodiment, of the bipolar type, having a tip electrode 28 at its distal end, and a ring electrode 30 spaced proximally back from the distal end. Tip electrode 28 and ring electrode 30 are coupled to separate, insulated lead conductors (not shown in FIG. 1) which extend along the length of lead body 12. The lead conductors function to electrically couple electrodes 28 and 30 to circuitry within the pulse generator. Lead conductors are concentric multi-filar coils made from MP35N wire.

Turning now to FIG. 2, there is shown a greatly enlarged cross-sectional side view of the distal end of lead 10 in accordance with the presently disclosed embodiment of the invention, including a distal portion of lead body 12, electrode and fixation assembly 26 and ring electrode 30.

As shown in FIG. 2, lead body 12 comprises an outer insulative sheath 32 made of silicone rubber, polyurethane, or the like. In the preferred embodiment, if sheath is made of silicone, then internal surface is treated to decrease friction, such as using the treatment disclosed in the co-pending U.S. patent application Ser. No. 08/239,007 entitled "Plasma Process for Reducing Friction Within the Lumen of Polymeric Tubing" of Stewart et al. Within outer insulative sheath 32 is inner conductor 34. Inner conductor 34 extends along the length of lead body 12 and terminates at its distal end where it is electrically coupled, for example by spot or laser welding, to an electrically conductive tube 37. Tube 37 functions as the substrate upon which porous, platinized sintered tip electrode 28 is formed. Tip electrode 28 is preferably constructed of a porous, sintered platinum having a porosity in the range of 0.5 to 100 microns. The porous platinum electrode material is further electroplated with platinum black. The platinum black coating is intended to reduce source impedance and polarization. In addition to functioning as the substrate for electrode 28, tube 37 is also preferably hollow, such that a substantially cylindrical chamber 43 is defined directly behind porous electrode 28. Chamber 43 may then house a steroid-impregnated monolithic controlled released device (MCRD) 45 making electrode 28 steroid eluting. The steroid is also deposited with the pores of the tip electrode 28 as is well known in the art. Further details regarding the construction and loading of steroid into a MCRD and a tip electrode may be found in the U.S. Pat. No. 5,282,844 issued to Stokes, et al.

With continued reference to FIG. 2, outer sheath 32 also covers a second outer conductor 38 which electrically connects to ring electrode 30. Outer conductor 38 is preferably coiled concentrically with respect to inner conductor 34 and is electrically insulated therefrom by inner sheath 40.

The electrical and mechanical coupling between tube 37 and inner conductor 34 is facilitated by core element 44, as shown in FIG. 2. Tube 37 and core element 44, in turn, are disposed within a sleeve 36.

Figure 4:
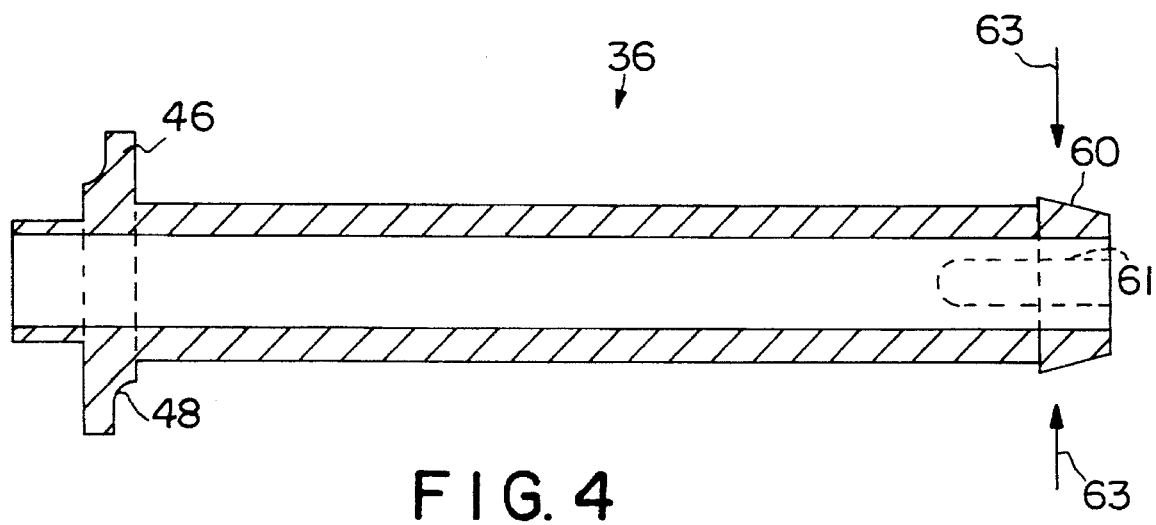
FIG. 4 is an enlarged side view of a sliding sleeve member used in the lead shown in FIGS. 2 and 3.
Figure 5:
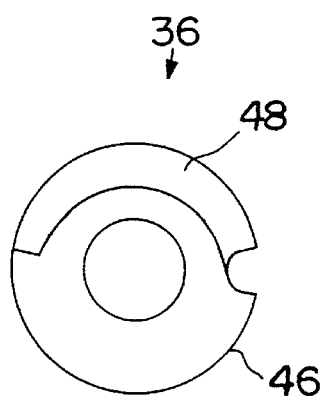
FIG. 5 is an enlarged end view of the sliding sleeve member from FIG. 4.

In FIGS. 4 and 5, there are shown enlarged side and end views, respectively, of sleeve 36 from electrode assembly 26, shown in isolation. Sleeve 36 is substantially cylindrical, and is, in the presently preferred embodiment of the invention, made of molded, annealed polyurethane. As shown in FIG. 4, sleeve 36 is provided with a helix-engaging collar 46 substantially near its distal end. Collar 46 has helical groove 48 which conforms to the size and shape of a fixation helix 50 disposed at the distal end of electrode assembly 26, as shown in FIG. 2. As can be seen in FIG. 2, groove 48 enables collar 46 to engage helix 50 in a screw-like fashion, such that when helix 50 is rotated with respect to sleeve 36, helix 50 is relatively advanced or retracted.

As shown in FIG. 2, helix 50 is coupled to a helix end cap 52 with reinforcement band 51. Helix end cap 52, in turn, is mounted on and mates with a molded seal retainer 54. Seal retainer 54 and helix end cap 52 interlock as shown in FIG. 2 so as to retain a substantially annular slide seal 56 therein. In the presently preferred embodiment, helix end cap 52, reinforcement band 51 and seal retainer 54 are made of molded polyurethane or the like, while slide seal 56 is made of silicone rubber. By pressing against the outer surface of sleeve 36, slide seal 56 functions to prevent leakage of body fluids into electrode assembly 26, while at the same time allowing sleeve 36 to slide and rotate within electrode assembly 26 (i.e., in the directions indicated by double-ended arrow 58 in FIG. 2.)

Sleeve 36 also preferably is provided with a flared portion 60 at its proximal end limit the extent of forward (distally-directed) travel of sleeve 36. In addition, sleeve 36 preferably has notches 61 in its proximal end (see FIG. 4), for allowing compression of flared portion 60 in the direction of arrows 63 to facilitate assembly of electrode assembly 26.

The coupling of electrode assembly 26 to the distal end of lead body 12 is accomplished by securing seal retainer 54 to outer sheath 32 by means of medical adhesive bonding material 55. As shown in FIG. 2, the distal end of seal retainer 54 may be implemented with circumferential ridges 57 to enhance the bonding with outer sheath 32.

Figure 6:
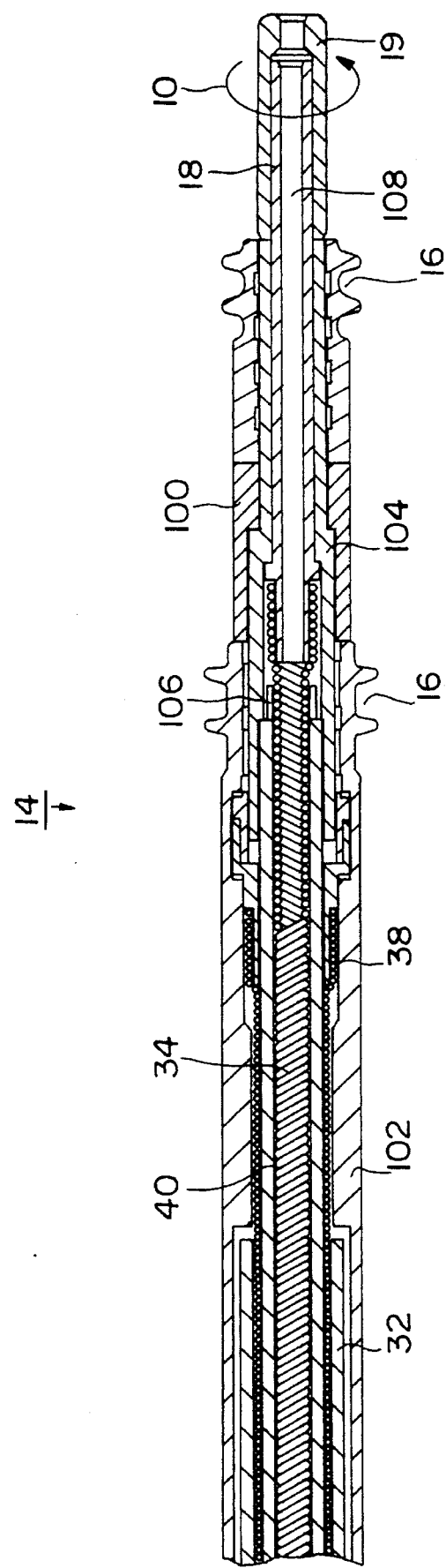
FIG. 6 is an enlarged cross-sectional view of the terminal assembly on the proximal end of the lead from FIG. 1.

As previously noted, a terminal assembly 14 is disposed at the proximal end of lead body 12. In FIG. 6 there is shown a greatly enlarged cross-sectional view of a preferred implementation of terminal assembly 14. With reference to FIG. 6, terminal assembly 14 comprises a terminal pin 18 (shown in FIG. 6 covered with a terminal pin cap 19) and sealing rings 16. Terminal pin 18 facilitates an electrical connection between inner conductor 34 and a terminal in the connector block of pulse generator, in accordance with common practice in the art. Terminal assembly 14 additionally comprises a second, ring-like connector, designated with reference numeral 100 in FIG. 6, for facilitating an electrical connection between outer conductor 38 and a terminal in the connector block of a pulse generator, also in accordance with common practice in the art.

In FIG. 6, inner sheath 40 and outer sheath 32 are also shown. In addition, a molded seal and strain relief collar, designated with reference numeral 102 covers a proximal portion of lead body 12. Collar 102 is preferably made of silicone rubber or the like and is provided to seal terminal assembly 14 from the in vivo environment, and to lessen strain on conductors 34 and 38 by preventing extremely sharp bending of the lead body at the connection to terminal assembly 14. As shown in FIG. 1, strain relief collar 102 extends along only a proximal portion of lead body 12.

In accordance with one aspect of the present invention, certain parts of terminal assembly 14 are capable of axial rotation independently of other parts of terminal assembly 14. In particular, connector pin 18 and connector pin cap 19 are rotatable with respect to a connector pin retainer 104 through which connector pin 18 extends. Inner conductor 34, by virtue of being coupled to connector pin 18, also is able to rotate within inner sheath 40. Annular bearing 106 supports inner conductor 34, during such rotation.

Terminal pin 18 has a longitudinal lumen 108 along its length, such that a stylet may be inserted through terminal pin and into the lumen defined by the coils of inner conductor 34, in accordance with common practice in the art.

As thus far described, it will be apparent to those of ordinary skill in the art that the configurations of electrode assembly 26 and terminal assembly 14 are such that terminal pin 18, inner conductor 34 and sleeve 36 can be held in a fixed position while inner sheath 40, outer conductor 38, outer sheath 32, helix 50, helix end cap 52 and seal retainer 54 are axially rotated (i.e., rotated in the direction of arrow 110 in FIGS. 3 and 6). As a result of such rotation in one direction, helix 50 is caused to advance distally out, in a screw-like fashion, due to its engagement with helix engaging collar 46, to the position shown in FIG. 3. Rotation in the opposite direction causes helix 50 to retract proximally in, to the position shown in FIG. 2.

(For the sake of consistency in the present description, the proximal and distal movement of helix 50 with respect to sleeve 36 and helix engaging collar 46 will be referred to as the retraction or advancement of helix 50 proximally or distally, due to screw-like engagement of helix 50 with helix engaging collar 46. It would, however, be equally accurate to describe this relative motion as a proximal or distal motion of sleeve 36 with respect to helix 50. This convention is adopted because, as will be hereinafter described in further detail, fixation of helix into myocardial tissue involves rotation of outer components, including helix 50, outer sheath 32, etc . . . , while inner components, including inner conductor 34, sleeve 36 and helix engaging collar 46, are held stationary.)

As depicted in FIG. 2, helix 50 is retracted as far proximally as possible (or, sleeve 36 is advanced as far distally as possible), with further proximal retraction of helix 50 (or distal extension of sleeve 36) being prevented by flared proximal end portion 60 of sleeve 36 coming into contact with a reduced inner diameter of seal retainer 54 at a point designated 62 in FIG. 2. When helix 50 is fully retracted as shown in FIG. 2, porous sintered electrode 28 projects distally beyond the coils of helix 50 and collar 46 is engaged substantially near the distal end of helix 50. This arrangement advantageously facilitates introduction of lead 10 into a patient's venous system, since fixation helix 50 is effectively prevented from engaging or otherwise becoming snagged on a venous wall as the lead is advanced. In addition, once lead 10 has been introduced, the fact that tip electrode 28 projects distally beyond the coils of helix 50 enables tip electrode 28 to be held in contact with endocardial tissue at a proposed fixation site. That is, the exposure of tip electrode 28 when sleeve 36 is fully distally advanced enhances the mappability of the lead, as previously discussed.

In the embodiment of FIG. 2, relative retraction of helix 50 with respect to tip electrode 28 is accomplished by holding inner components, including terminal pin 18, inner conductor 34 and sleeve 36 stationary, while outer elements, including inner sheath 40, outer conductor 38, outer sheath 32, helix end cap 52 and seal retainer 54 are rotated in a first direction. Likewise, distal advancement or extension of helix 50 is accomplished by holding the aforementioned inner components stationary, while the aforementioned outer components are rotated in a second direction, opposite from the first, so that helix 50 is drawn in a screw-like fashion distally outward to a position of maximum extension, such as is depicted in FIG. 3. When fully extended as shown in FIG. 3, tip electrode 28 is positioned within the coils of helix 50, rather than being positioned distally beyond the coils of helix 50 as in FIG. 2. That is, the coils of helix 50 are exposed, such that helix 50 may be screwed into cardiac tissue in accordance with common practice in connection with prior art "screw-in" leads.

Figure 7:
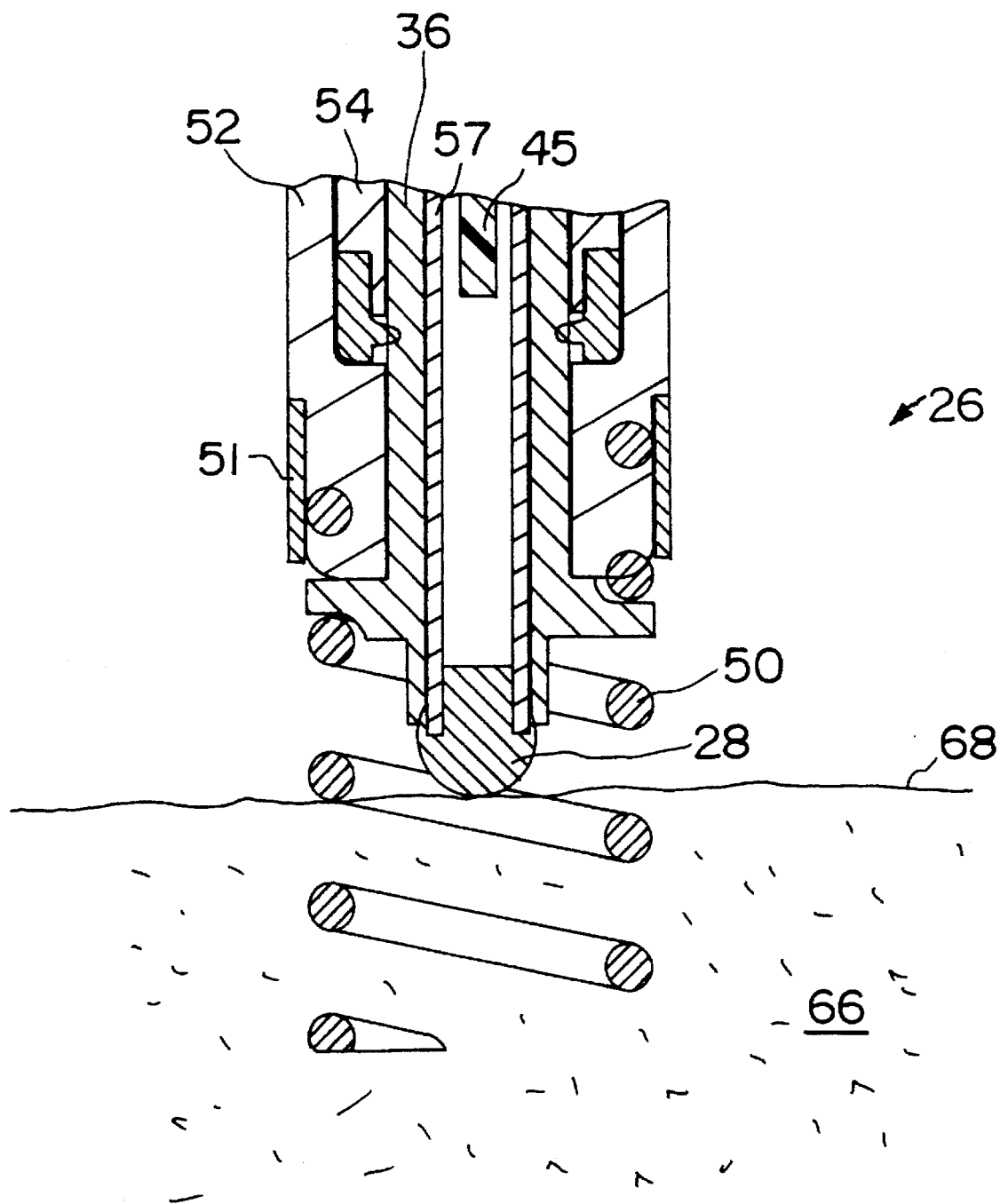
FIG. 7 is an enlarged side view of the lead from FIG. 1 with the electrode assembly having been screwed into endocardial tissue.

Referring to FIG. 7, there is shown an enlarged illustration of the distal end of electrode assembly after helix 50 has been screwed into endocardial tissue 66 as described above. During introduction of lead 10 into the patient, helix 50 is placed in the fully retracted position of FIG. 2, such that the tip of helix 50 is protected by collar 46 and thereby prevented from catching or tearing the venous wall as lead 10 is advanced through the venous system in a conventional manner. When electrode assembly arrives at a potentially desirable fixation site (for example, through conventional fluoroscopic techniques) the site's electrical characteristics can be assessed (mapped), since tip electrode 28 extends out beyond the end of helix 50. Once the site is determined to be suitable, outer components of lead 10, including outer sheath 32, seal retainer 54, helix end cap 52 and helix 50, are rotated in the direction of arrow 110, while inner components of lead 10, including terminal pin 18, inner conductor 34, sleeve 36 and helix engaging collar 46 are held stationary, in a manner to be hereinafter described, so that helix 50 advances distally beyond helix engaging collar 46, to the position shown in FIG. 3. As helix 50 rotates and advances distally outward, it screws into tissue 66. As shown in FIG. 7, helix is preferably screwed far enough into tissue that electrode 28 is brought into contact with and held against tissue interface 68.

As noted above, one feature of the presently disclosed embodiment of the invention is that outer components of lead 10, including outer sheath 32, inner sheath 40, seal retainer 54, helix end cap 52 and helix 50 are rotatable about the longitudinal axis of lead 10 independently of inner components including terminal pin 18, inner conductor 34, sleeve 36 and helix engaging collar 46.

To cause helix 50 to advance or retract as described above, it is necessary to provide some means for holding inner components, including terminal pin 18, inner conductor 34, sleeve 36 and helix engaging collar 46 relatively stationary while applying rotational force is applied to the outer components, including outer sheath 32. To this end a so-called "steerable" stylet may be used to engage inner conductor 34 substantially at or near its distal end, so that when the outer components are rotated, helix engaging collar 46 is held stationary, causing helix 50 to advance or retract (depending upon the direction of rotation).

Figure 8:
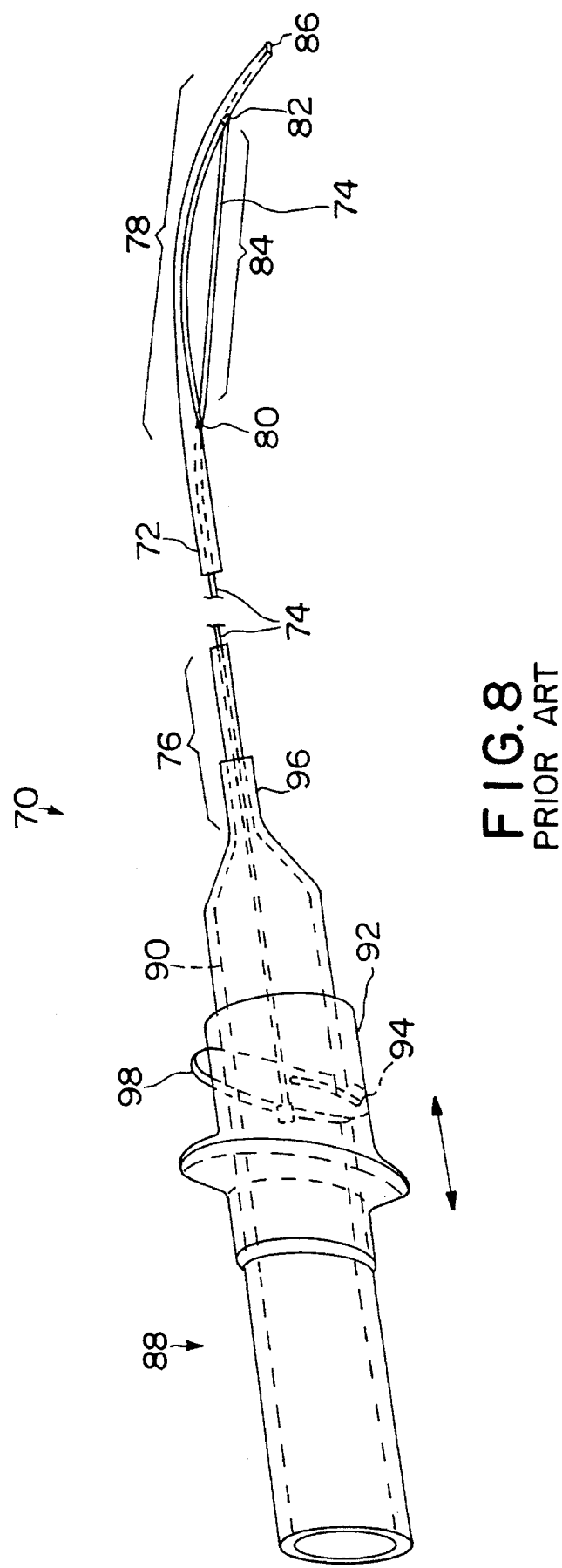
FIG. 8 a perspective view of a steerable stylet and manipulable handle assembly used to advance and retract the electrode assembly of the lead from FIG. 1.

A suitable steerable stylet is disclosed in detail in co-pending U.S. patent application Ser. No. 08/069,310 filed in the name of Brennen et al. and entitled "Steerable Stylet and Manipulative Handle Assembly", hereby incorporated by reference herein in its entirety. For the sake of clarity of the present disclosure, an illustration of the steerable stylet in accordance with the Brennen et al. disclosure is provided in FIG. 8 herein. Referring to FIG. 8, a steerable stylet and manipulable handle assembly 70 comprises an elongated tubular member 72 and a pull wire 74 having a proximal section 76 and a distal section 78 with an elongated intermediate section extending therebetween (not specifically illustrated in FIG. 8). Distal section 78 includes first and second apertures separated by a distance 84 which is preferably in the range of two to four inches, including the distal straight section extending between second aperture 82 and the extreme distal tip 86 of stylet 70.

From distal end 86, pull wire 74 extends within the internal lumen of tubular member 72, out second aperture 82 and alongside tubular member 72 along the section 84, whereupon it extends into first aperture 80 and proximally through the lumen of tubular member 72 to proximal section 76. Pull wire 74 is only fixedly attached to tubular member 72 at distal end 86.

Handle 88 includes a housing 90, a slide member 92 and a spring wire clip element 94. Tubular member 72 is mechanically attached to a neck portion 96 of handle 88.

Pull wire 74 extends within housing 88 and is mechanically coupled to a lever 98 therein. In use, lever 98 is used to draw slide member 92 back, thereby exerting a tractional (i.e., proximally directed) force upon pull wire 74. Those of ordinary skill in the art having the benefit of this and the above-referenced Brennen et al. disclosure will appreciate that the configuration of pull wire 74 in the distal section 78 of tubular member 72 is such that the pulling force upon pull wire 74 causes a controlled bending or curvature of distal section 78, the extent of curvature being determined by the amount of tractional force applied to pull wire 74.

In the Brennen et al. disclosure, steerable stylet 70 is described as being utilizable for imparting a controlled amount of curvature to the distal end of an implantable lead into which it is inserted, thereby facilitating steering the lead through a patient's venous system to a desired implantation site. It is contemplated, however, that in addition to being useful in this capacity, steerable stylet 70 will also be effective in engaging the inner conductor of a lead substantially at the distal end of the lead, by virtue of section 84 of pull wire 74 being pressed against the lumen defined by the coiled inner conductor of the lead. As a result, steerable stylet 70 may be used to hold inner components of lead 10, including inner conductor 34, sleeve 36, and helix engaging collar 46 relatively stationary, while outer components are rotated to screw helix 50 into cardiac tissue.

In another embodiment of the invention, a slotted-tipped (i.e., "screwdriver-tipped") stylet may be used to hold inner conductor 34 (and hence, sleeve 36 and helix engaging collar 46) stationary. Slotted-tipped stylets are conventional and well-known in the implantable lead art, such as that disclosed in the U.S. Pat. No. 4,350,169 to Dutcher et al.

From the foregoing detailed description of a specific embodiment of the invention, it should be apparent that an implantable screw-in endocardial lead having enhanced mappability and fixation characteristics has been disclosed. Although a specific embodiment of the invention has been disclosed herein in some detail, this has been done merely to illustrate the invention in various of its features and aspects and is not intended to be limiting with respect to the scope of the invention as defined by the claims, which follow. It is contemplated that various substitutions, alterations and/or modifications, including but not limited to those specifically noted herein, may be made to the embodiment of the invention disclosed herein without departing from the spirit and scope of the invention as defined by the claims.

What is claimed is:

1. A body-implantable, electrically-conductive lead comprising:

a flexible, elongate lead body having an outer surface defined by a tubular outer sheath having a lumen extending along its longitudinal axis from its proximal end to its distal end;

a tubular inner sheath having a lumen extending along its longitudinal axis from its proximal end to its distal end, the inner sheath being coaxially disposed within the outer sheath's longitudinal lumen and being substantially coextensive with the outer sheath and rotatable within the outer sheath about its longitudinal axis;

a first coiled conductor, disposed within the outer sheath and coiled around the inner sheath, extending from the proximal end of the outer sheath to a ring electrode disposed at a point spaced back from the outer sheath's distal end; and a second coiled conductor, disposed within the inner sheath and extending from the proximal end of the inner sheath to a tip electrode, the second coiled conductor being axially rotatable independently from the first coiled conductor;

an electrode assembly coupled to the distal end of the lead body, the electrode assembly comprising a helix end cap rigidly coupled to the outer sheath, and a fixation helix coupled to the helix end cap;

a substantially cylindrical sliding sleeve slidably projecting through a longitudinally-oriented lumen in the helix end cap, the sliding sleeve electrically coupled to the second coiled conductor, the sliding sleeve having proximal and distal ends and having a helix-engaging collar substantially near its distal end, engaged in a screw-like manner in the helix;

the tip electrode is disposed on the distal end of the sliding sleeve, and disposed within the helix.

2. A lead in accordance with claim 1, further comprising a substantially annular seal disposed in the longitudinally-oriented lumen of the end cap, for preventing seepage of body fluids through the helix end cap lumen into the electrode assembly and also allowing sleeve to slide and rotate within electrode assembly.

3. A method of implanting an elongate body-implantable transvenous endocardial lead having an outer tubular sheath with proximal and distal ends and a fixation helix rigidly disposed on the distal end thereof, the lead further having an inner coiled conductor, substantially coextensive with the outer tubular sheath and rotatable about a longitudinal axis thereof independently of the outer tubular member to cause distal advancement or proximal retraction of the fixation helix with respect to an electrode assembly coupled to the inner conductor and engaged in a screw-like fashion within the fixation helix, the method comprising the steps of:

(a) holding the conductor stationary while axially rotating the outer sheath and fixation helix in a first direction to retract the helix to a fully retracted position;

(b) introducing the lead into a patient's venous system such that the electrode assembly reaches a desired fixation site; and (c) holding the conductor stationary while axially rotating the outer sheath and fixation helix are axially rotated in a second direction to advance the helix distally forward to a fully advanced position and to screw the helix into the fixation site.

4. A method in accordance with claim 3, wherein the steps (a) and (c) of holding the conductor stationary while rotating the helix comprise the sub-step of inserting a stylet adapted to engage the conductor substantially near a distal end thereof into the lead from the proximal end thereof.

5. A medical electrical lead having a connector assembly, a lead body coupled to the connector assembly, the lead body having a conductor and an insulative sleeve insulating the conductor, the conductor being rotatable within the insulative sleeve, the medical electrical lead further having an electrode and fixation assembly connected to a distal end of the lead body, the electrode and fixation assembly comprising:

a fixation helix attached to the distal end of the lead body, the fixation helix having an inner lumen and a distal tip; and a sleeve attached to the distal end of the lead body, the sleeve positioned within the inner lumen, the sleeve movable between a first position wherein the sleeve is wholly within the inner lumen and a second position wherein an end of the sleeve extends beyond the distal tip of the fixation helix, the sleeve having means for helically engaging the fixation helix.

* * * * *